United States Patent [19]

Yum

[11] Patent Number: 5,024,663
[45] Date of Patent: Jun. 18, 1991

[54] SELF-CONTAINED SUCTION PUMP

[75] Inventor: Su Il Yum, Los Altos, Calif.

[73] Assignee: Alza Corporation, Palo, Calif.

[21] Appl. No.: 482,572

[22] Filed: Feb. 21, 1990

[51] Int. Cl.⁵ ............................................. A61M 37/00
[52] U.S. Cl. .................................... 604/131; 604/141
[58] Field of Search .............. 604/131, 132, 141, 151, 604/153, 51, 52, 53, 93

[56] References Cited

U.S. PATENT DOCUMENTS

| | | | |
|---|---|---|---|
| 3,584,770 | 6/1971 | Taylor | 604/141 |
| 3,760,984 | 9/1973 | Theeuwes | 222/95 |
| 3,838,794 | 10/1974 | Coglax et al. | 604/141 |
| 3,845,770 | 11/1974 | Theeuwes et al. | 128/260 |
| 3,865,108 | 2/1975 | Hartop | 128/260 |
| 3,880,164 | 4/1975 | Stepno | 128/276 |
| 3,895,631 | 7/1975 | Buckles et al. | 128/213 |
| 3,987,790 | 10/1976 | Eckenhoff et al. | 128/260 |
| 4,034,756 | 7/1977 | Higuchi et al. | 128/260 |
| 4,299,222 | 11/1981 | Eckenhoff et al. | 128/278 |
| 4,474,575 | 10/1984 | Eckenhoff et al. | 604/131 |
| 4,573,992 | 3/1986 | Maral et al. | 604/141 |
| 4,741,733 | 5/1988 | Winchall | 604/132 |
| 4,769,008 | 9/1988 | Hessal | 604/132 |
| 4,820,273 | 4/1989 | Reinicke | 604/141 |
| 4,913,702 | 4/1990 | Yum et al. | 604/131 |
| 4,929,233 | 5/1990 | Roth et al. | 604/131 |

FOREIGN PATENT DOCUMENTS

949513  6/1974  Canada ................................ 222/80

Primary Examiner—Paul J. Hirsch
Attorney, Agent, or Firm—Jacqueline S. Larson; Edward L. Mandell; Steven F. Stone

[57] ABSTRACT

The present invention is directed to a self-contained suction pump for drawing a fluid, such as a sample of biological fluid from an animal body, and to a method for obtaining a fluid sample. The present invention is particularly useful for repetitive or continuous collection of a series of samples over a period of time.

20 Claims, 4 Drawing Sheets

SELF-CONTAINED SUCTION PUMP

FIELD OF THE INVENTION

This invention relates to a self-contained suction pump for drawing samples of fluid.

BACKGROUND OF THE INVENTION

Many phases of basic physiology research, clinical research, and clinical diagnostic practice require repetitive sampling of body fluids for assay of key components. While sampling may be accomplished by repeated skin or tissue puncture, use of a catheter or cannula may be preferable in order to minimize trauma to the subject and the fluid source. Trained attendants are required for withdrawal of each timed sample, catheter flushing, and sample processing as each is collected. Knowledge of the time-course of changes in measured constituents is required to ensure that interpolation of intermittent results represents true patterns. However, continuous sampling may be acceptable or even preferred in some situations, such as in determination of total hormone secreted over time or when secretion dynamics are so rapid or erratic that punctate sampling might not capture significant changes in constituent levels. In such cases, constant withdrawal pumps can be employed, and sampling does not require constant supervision. However, these pumps are too bulky to be carried during normal activities, and the subject must be relatively immobile in order to avoid tangling the catheter. This constraint may alter hormone secretion patterns due to perturbation of the subject's lifestyle. Sophisticated miniaturized pumps with cooled sampling chambers are useful in clinical research to minimize such disturbances, but their cost precludes their use for routine diagnostic work or basic research.

U.S. Pat. No. 4,299,222 describes a self-contained suction pump consisting of an outer impermeable expansible housing, an inner collapsible elastomeric fluid collection container, a rigid semipermeable partition between the housing and the container and a water-imbibing composition interposed between the housing and the partition. The pump is activated by charging an aqueous fluid between the partition and the container. The water-imbibing composition takes up the fluid and creates hydrostatic pressure, thereby forcing the housing to expand outwardly. The evacuation of the water from between the partition and the container permits the container to expand, which creates a suction to draw liquid from an outside source into the container. However, only a small sample can be obtained at one time with this pump.

U.S. Pat. No. 3,880,164 describes an osmotically driven device for evacuating fluids from body cavities or wounds. The device comprises a fluid collection container that is divided into two compartments by a flexible water-impermeable partition and a semipermeable conduit that connects to one of the container compartments and extends to the fluid collection site. The conduit and the container compartment to which it is connected contain a solution that has a higher osmotic pressure than the body fluid to be collected. The other compartment is empty. Body fluids are drawn into the conduit and hence into the solution-filled compartment by osmosis. The influx of fluid causes the partition to displace into the empty compartment, thereby accommodating the incoming water.

Fluid-imbibing positive action pumps that dispense liquids rather than collecting them are described in U.S. Pat. Nos. 3,987,790 and 4,034,756. A commercial embodiment of the pumps described in these patents is marketed as the ALZET ® minipump. The pumps consist of an outer rigid semipermeable housing, an inner collapsible bag contained within the housing and an osmotically effective solute interposed between the housing and the inner bag. Liquid to be dispensed is charged into the inner bag and the minipump is placed in a water-containing environment. Water from the environment diffuses through the housing and dissolves the solute. The osmotic pressure imbalance between the resulting solution and the water in the environment causes water to be imbibed through the housing into the space between it and the bag. This influx of water exerts pressure on the bag, causing it to collapse and the liquid charge to be squeezed therefrom through an outlet port.

Other fluid imbibing pumps for dispensing liquids are described in U.S. Pat. No. 3,845,770, in which an osmotically active solute is contained within a rigid, semipermeable membrane provided with an outlet. This pump is activated by placement in a fluid environment. However, this pump does not employ a collapsible or movable element to expel its contents; instead, as the fluid passes through the semipermeable membrane, the solute is dissolved and the saturated solution formed is pressurized as a result of the osmotic pressure generated within the semipermeable membrane. A commercial embodiment of such pumps is marketed as the OROS ® elementary osmotic pump.

U.S. Pat. No. 4,474,575 discloses a self-driven pump assembly for dispensing a small amount of a liquid for a prolonged period of time. The pump assembly comprises a fluid imbibing pump, such as an ALZET or an OROS pump, mounted within a receptacle into which actuating fluid is placed. The liquid to be dispensed is contained within the fluid imbibing pump, and the fluid-filled receptacle provides the water-containing environment required for actuation of the pump, as described above for the ALZET and the OROS pumps.

Despite the development of the art, however, there remains a need to develop a pump for collecting a series of fluid samples over a period of time that is simple to use, portable, inexpensive, and does not interfere with the normal activities of the donor.

SUMMARY OF THE INVENTION

The present invention is directed to a self-contained suction pump for drawing a fluid, such as a sample of biological fluid from an animal body, and to a method for obtaining a fluid sample. The present invention is particularly useful for repetitive or continuous collection of a series of samples over a period of time. The components of the pump are:

a) an impermeable rigid housing;
b) a fluid imbibing means sealingly mounted within the housing and having an external surface which is at least in part permeable to an actuating fluid;
c) a space between the outer wall of the fluid imbibing means and the inner wall of the rigid housing adapted to contain an actuating fluid;
d) an injection port for injecting an actuating fluid in the space between the housing and the fluid imbibing means;
e) a suction port extending through the rigid housing and in communication with the space between the housing and the fluid imbibing means; and f) sample receiving means adapted to be attached to the suction port and to a fluid sample source.

In the practice of the invention, the suction pump is activated by charging an actuating fluid into the space between the inner wall of the housing and the outer wall of the fluid imbibing means. The charged actuating fluid permeates through the outer membrane of the fluid imbibing means. As the actuating fluid is displaced from the space into the fluid imbibing means, a suction is exerted to draw sample fluid into the sample receiving means from a sample source.

DETAILED DESCRIPTION OF THE INVENTION

As used herein, the term "fluid imbibing means" encompasses any device or means which imbibes or otherwise takes up and holds an actuating fluid over an extended period of time upon contact with the actuating fluid.

In the following discussion, like reference numerals refer to like elements in the figures.

Figure 1:
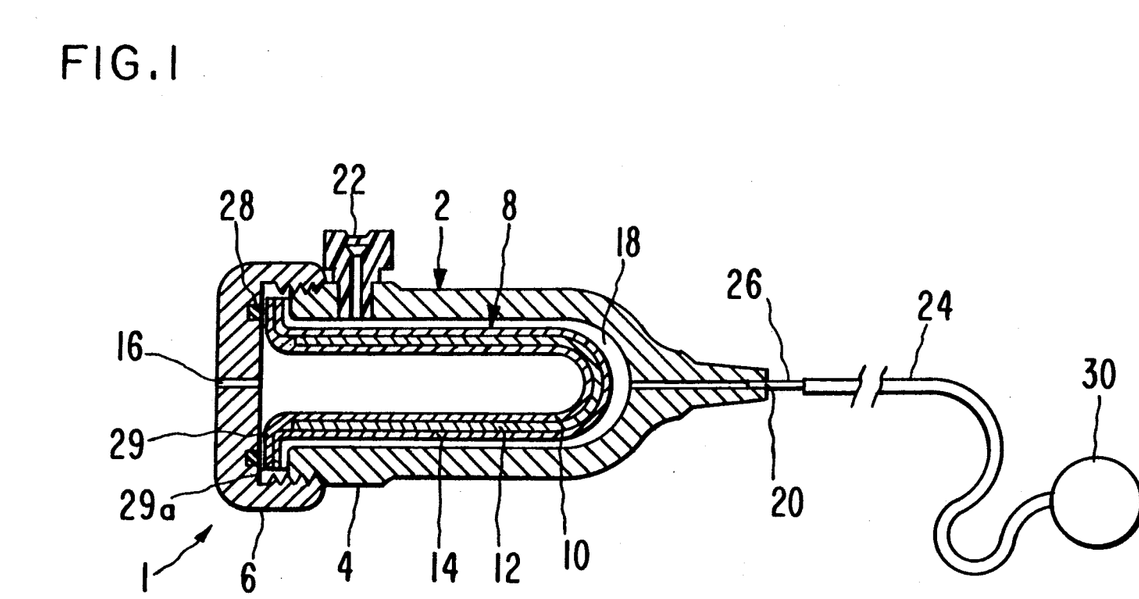
FIG. 1 is a cross-sectional view of one embodiment of the suction pump of the invention.

One embodiment of the pump of the invention is illustrated in FIG. 1, which shows the basic elements of the suction pump, numbered generally as 1. The elements are an impermeable rigid housing 2 comprised of a body 4 and a screwably attached cap or lid 6 enclosing one end of the housing; a fluid imbibing means which in this embodiment comprises a driving member 8 and includes an inner flexible bag 10, an intermediate layer 12 of an osmotically effective solute encapsulating the bag 10, and an outer shape-retaining membrane 14 encapsulating the solute layer 12; a vent or bore 16 through cap 6 and in communication with the interior of driving member 8 to provide a passageway from the interior of the driving member to the exterior of the housing; a space 18 between the inner wall of the body 4 of the rigid housing 2 and the outer wall of the driving member 8; a suction port 20 through body 4 at a position opposite from vent 16 and in communication with space 18 to provide a passageway from the space to the exterior of the housing; injection port 22 extending through body 4 and in communication with space 18; and a sample receiving means which in this embodiment comprises a tubular member 24 for receiving body fluids from a sample source 30, the tubular member being connected to the suction port 20 by a connector 26. Connector 26 may conveniently be a blunt-tip needle with attachment hub for attaching to the suction port 20.

Body 4 and cap 6 of the housing 2 are formed of any rigid, impermeable water- and air-tight material. Such material may be selected from suitable plastics or metals such as, for example, polystyrene, polyethylene, polypropylene, polyvinyl chloride, reinforced epoxy resin, polymethylmethacrylate, etc., sheet metal (e.g., aluminum, copper, steel, etc.), galvanized pipe, or styrene/acrylonitrile copolymer. A preferred embodiment of the invention is directed to a housing 2 that is reusable, that is, it can be repeatedly opened and closed to insert and replace a fluid imbibing means. While a screwable cap is illustrated in FIG. 1, any removable and resealable closure may be used to seal the housing, such as a snap lid or a plug. The only requirements of the closure are that it allow placement and removal of a fluid imbibing means in the body 4 and that it create a seal with body 4 that is water- and air-tight. In FIG. 1, a ring gasket 28 is present in cap 6 to form a seal with body 4 to provide water- and air-tightness.

Bag 10 may be made of any material that is flexible and impermeable to the solute composition of layer 12. Bag 10 may be made, for example, from elastomeric compositions that may be formed into thin sheets. The elastomeric properties of the bag composition and the thickness of the bag wall should be such as to cause the bag to readily collapse inwardly when a force is applied to the bag exterior. Typical examples of such compositions are disclosed in commonly owned U.S. Pat. No. 3,760,984 and in commonly owned Canadian Pat. No. 949,513, the disclosures of which are incorporated herein by reference. While the shape and size of bag 10 is not limited, bag 10 is open at the end that is in communication with vent 16.

Bag 10 is at least partly encapsulated by layer 12 of an osmotically effective solute composition. The purpose of layer 12 is to imbibe water across membrane 14 into the space between the exterior of bag 10 and the inner surface of membrane 14, that is, the space occupied by layer 12. Thus, suitable solutes exhibit an osmotic pressure gradient against an external fluid across the semipermeable membrane 14. Various osmotically effective solute compositions are disclosed in U.S. Pat. Nos. 3,760,984 and 4,034,756, incorporated herein by reference.

Solute layer 12 is in turn encapsulated by outer membrane 14. The outer surface of membrane 14 defines the outer wall of driving member 8. At least a part of membrane 14 is permeable to water, and preferably all of membrane 14 is water-permeable. At the same time, membrane 14 is impermeable to the osmotically effective solute composition of layer 12. Membrane 14 is also shape-retaining, that is, it is sufficiently rigid to be substantially undeformed as water is injected into space 18 between the outer surface of membrane 14 and the inner surface of body 4, or by the hydrostatic pressure that is generated in the space between the inner surface of membrane 14 and the exterior surface of bag 10 by the water imbibed by solute layer 12. The thickness and composition of membrane 14 affects the rate at which water will be imbibed through it by solute layer 12. Such membranes and compositions that may be used to form them are disclosed in said U.S. Pat. No. 3,760,984 and in said Canadian Pat. No. 949,513.

The driving member 8 is attached to housing 2 by any suitable means. As illustrated in FIG. 1, as one example, the flexible bag 10 and membrane 14 may extend beyond their attachment with layer 12 to provide solute- and actuating fluid-impermeable flaps or lips 29 and 29a which extend over the edge of body 4 and are in sealable relation with body 4 and cap 6.

Injection port 22 provides access to the interior of housing 2, that is, to space 18 between the inner wall of body 4 and the outer wall of driving member 8, for filling space 18 with an actuating fluid such as water. For this purpose, injection port 22 may be formed of a water-impermeable material that is penetrable by a hypodermic needle and self-sealing after withdrawal of the needle. Such materials are generally known to the art as elastomers, examples of which are disclosed in U.S. Pat. No. 3,760,984.

Space 18 must be of sufficient size to hold the amount of water necessary to cause imbibition by solute layer 12 for the entire sampling period desired.

The sample receiving means of the present invention is advantageously an elongated flexible tube, such as tubular member 24 in FIG. 1, that is adapted for attachment to a sample source 30, such as by means of a catheter or a cannula, for receiving and retaining the fluid sample. Tubular member 24 should be made of a flexible material that is impermeable to and is compatible with, that is, does not interact with, the fluid being collected. The tubular member is initially empty or may contain a material or materials, such as heparin for example, useful in the collection of the body fluid sample, such as blood for example. The length and/or diameter of the tubular member 24 should be of sufficient size to retain all of the fluid sample taken during the sampling period. Sample should not be allowed to pass through the tube and into the suction port 20 and the space 18. In other words, the internal volume of the sample receiving means must be greater than the volume of fluid to be sampled.

Figure 3:
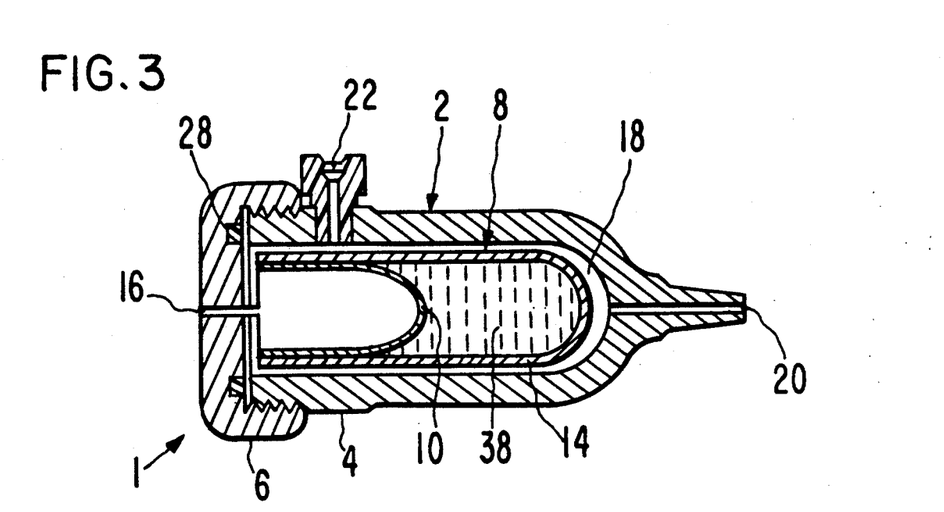
FIG. 3 is a cross-sectional view of a third embodiment of the suction pump of the invention.

In an alternative embodiment of the invention, illustrated in FIG. 3, the solute layer 12 is replaced by a solution 38 of an osmotically effective solute which occupies the volume of driving member 8 other than that occupied by flexible bag 10 and membrane 14. Solution 38 exhibits an osmotic pressure gradient against water in space 18. Solution 38 is preferably a saturated aqueous salt solution. To maintain the solution saturated and therefore to achieve a constant osmotic pressure throughout operation of the pump, excess solute in solid form is preferably present with solution 38. Various osmotically effective solutes can be used, as discussed hereinabove. The excess solid solute can be in the form of dispersed particles or in the form of a pellet. The solution can initially be a solution of the same osmotically effective solute or of an osmotically effective solute different than the solid excess solute.

In addition to the above embodiments, it is contemplated that any fluid imbibing pump structure which functions by the controlled imbibition of a fluid from an external source to generate a relatively constant internal pressure can be used as the fluid imbibing means of this invention. Preferred embodiments utilize pumps such as those disclosed and claimed in U.S. Pat. Nos. 3,987,790, 4,034,756 or 3,845,770, for example. Such devices are inexpensive and available as the ALZET ® minipump and the OROS ® elementary osmotic pump, both from ALZA Corporation, 950 Page Mill Road, Palo Alto, Calif.

Figure 2:
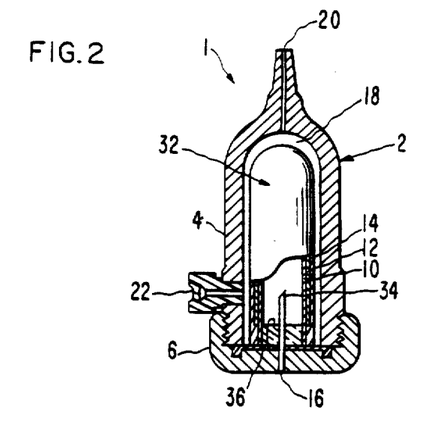
FIG. 2 is a partial cross-sectional view of another embodiment of the suction pump of the invention.

FIG. 2 shows one preferred embodiment of the invention where the driving member 8 is conveniently replaced by an ALZET ® minipump. The ALZET minipump 32 comprises a rigid semipermeable membrane 14 surrounding an osmotically effective solute 12 and an impermeable flexible rubber bag 10. A plug 36 formed of an elastomeric material seals the pump and may or may not be provided with a central port which is fitted around a blunted standard hypodermic needle (not shown). Because the minipump 32 is self-contained and sealed, it is necessary, if a central port and needle are not included, to form a vent communicating between the interior of the minipump and the exterior of the housing 2 for passage of air. This is accomplished by the use of a venting needle 34 to puncture the plug 36. Needle 34 is of sufficient length to extend completely through plug 36 and into the interior of the minipump 32. Needle 34 is attached to and extends through cap 6 to form a vent 16. Thus, in a preferred embodiment, the vent takes the form of a venting needle. In preparing the embodiment of FIG. 2 for use, venting needle 34 is inserted into the plug 36 of minipump 32 until the minipump comes to a stop against the screw cap 6. The minipump 32 is then inserted into the body 4 of the housing 2 and the housing is sealed shut.

Figure 4:
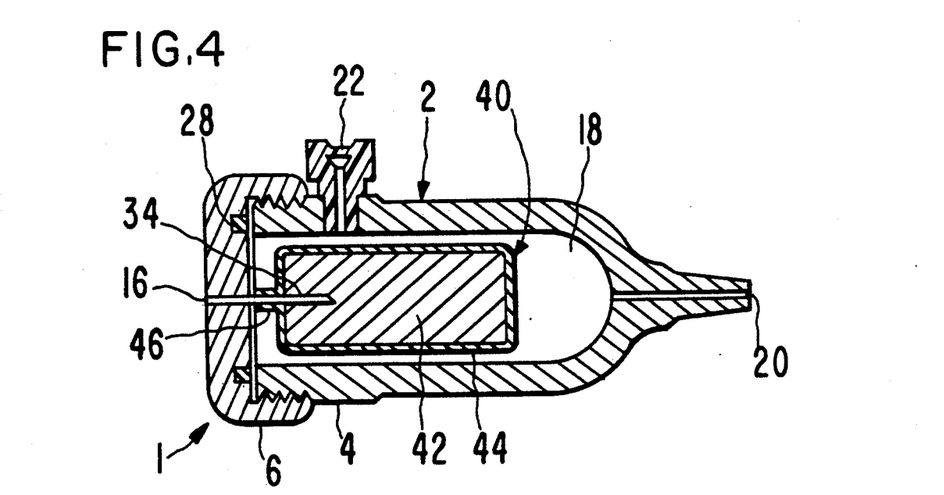
FIG. 4 is a cross-sectional view of a fourth embodiment of the suction pump of the invention.

Another embodiment of the invention is shown in FIG. 4, where the fluid imbibing means is an OROS ® pump 40, in which an osmotically active solute 42 is contained within a rigid, semipermeable membrane 44 provided with an outlet 46. A venting needle 34 of an external diameter smaller than the internal diameter of outlet 46 is inserted through outlet 46 and into the interior of the pump to provide an air passage.

The suction pump of the invention can be fabricated in any convenient shape. Dimensions of the device can thus vary widely and are not of controlling importance. The lower limit of the size of the device is governed by the amount of sample to be taken or by the period of time required for sampling. The size is also determined in part by the size of the fluid imbibing means used. For example, ALZET ® pumps may have overall dimensions as small as 1 cm. in length and 0.3 cm. in diameter.

Pump 1 is operated as follows, with reference to FIG. 1. The pump is activated by injecting water or other actuating fluid with needle and syringe through injection port 22 into space 18 between the housing body 4 and the fluid imbibing means 8, and filling that space with water or other actuating fluid from the syringe. The most convenient method for doing this is to place the pump in position as shown in FIG. 2, that is, with the cap 6 facing down and the suction port 20 facing up. Water is injected until excess water overflows from the suction port and no air bubbles remain. After space 18 is filled with water, the needle and syringe are removed and injection port 22, being made from an elastomer, seals itself. While the actuating fluid is preferably in the form of a low viscosity liquid, such as water, it is, however, contemplated that higher viscosity liquids or gels or a fluid absorbed onto a fibrous wick or porous mat could be used in certain embodiments as the source of actuating fluid for the fluid imbibing pump.

A desired length (and volume capacity) of tubing for the tubular member 24 is determined and cut for containing the fluid samples. The length of the tubing will be chosen depending on the travel speed of the sample in the tube, the duration of the desired sampling, and the volume of sample to be collected. The tubular member 24 is then attached to the suction port 20, by means of connecter 26, and to the sample source. Water from space 18 diffuses through outer semipermeable membrane 14 into the space occupied by solute layer 12. The water dissolves the osmotic solute within layer 12, and the osmotic pressure imbalance between the resulting solution and the water in space 18 creates influx of water across semipermeable membrane 14 into solute layer 12 and hence creates hydrostatic pressure therein, thereby forcing inner bag 10 to begin to collapse inwardly, displacing the air within the bag through and out the vent 16. The evacuation of water from space 18 into expanding layer 12 creates a suction within tubular member 24 which draws liquid from the sample source into tubular member 24.

After a desired volume of liquid sample is collected in the tubing and after a desired time interval of sample collection, the tube is clamped shut below the connector 26 and the tube is disconnected or cut from the connector and the sample source, with care not to allow the sample to escape. The sample is then drained into one or more containers for assay. The sample tube 24 may also be cut into several pieces and the pieces drained separately. Freezing the sample and tube makes this operation easier. Each piece of the tubing will contain the sample collected during different time intervals as estimated from the start-up time (i.e., the period of time needed for the pump to become fully activated) and the flow rate of the pump. The start-up time and sampling rate of the system will vary with temperature. The housing should be placed in a location which has a relatively constant temperature if a constant sampling rate is required.

Figure 5:
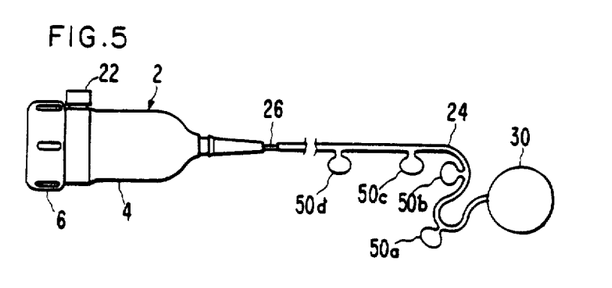
FIG. 5 is a side view of an embodiment of the invention.

In another embodiment for collecting time-sequential samples, the sample receiving means such as sample tubing 24 may be equipped with a plurality of sample reservoirs, such as reservoirs 50a, 50b, 50c and 50d shown in FIG. 5. Each reservoir would be filled, and thus sample collected, at a particular time interval. For example, sample reservoir 50a will fill at time $t_a$, sample 50b will fill at a later time $t_b$, and so forth. The intervals between the collection times $t_a$, $t_b$, $t_c$, etc., would depend on various factors such as the distance between the reservoirs and the volume of each reservoir in addition to those factors discussed previously above. The distances between the reservoirs may or may not be identical. Likewise, the volumes of the reservoirs may be the same or they may be different. To retrieve the collected samples for assay, after filling, each reservoir is closed off from the sample tubing 24, the reservoir is disconnected or cut from the tubing, and the sample is drained into a container.

The rate at which the suction pump draws a fluid sample can be varied from the maximum flow rate for which the fluid imbibing means is designed by providing means for varying the external area of the fluid imbibing means that is exposed to the actuating media. Also, it should be noted that while the prior art fluid imbibing pumps are actuated by water because of their being exposed to body fluid, according to this invention the actuating medium need not be water. The suction pump can contain any fluid which is non-destructive of the components, and the fluid imbibing means component is not dependent for actuation upon a liquid which is available within the body. Thus, while the pumps of the prior art have a nominal pumping rate normally established with respect to the rate at which body fluids are imbibed into the pump, the fluid imbibing means of this invention can be made to operate at pumping rates higher or lower than nominal by using fluids whose imbibition rate into the means is either higher or lower than body fluid. Thus, although the specific embodiments described herein relate to aqueous actuation, it should be recognized that these are merely preferred embodiments and are not limiting of the invention.

If commercially available pumps are used as the fluid imbibing means of this invention, they are available in a variety of sizes and with different sampling rates. For example, ALZET® minipumps are available which will move a fluid at the rate of 0.5 μl per hour for two weeks or 1 μl per hour for one week, based on actuation by an aqueous actuating fluid. Others are produced which move 2 ml of fluid over the same time periods. Thus, different ALZET minipumps may be chosen for different desired uses. See Table I, for example, for the nominal specifications applying to a system of the present invention which uses an ALZET (2 mL/15 hour) minipump and polyethylene 190 (PE 190) tubing having an internal diameter of 0.047 in. The Table also illustrates the effect of temperature on the system. Water is used as the actuating fluid for determining the rates in the Table.

TABLE 1

| Housing Temp (°C.) | Start-up Time (hrs) | Sampling Rate (ml/hr) | Sample Travel Speed in PE-190 (cm/hr) | Max. Duration of Use (hrs) |
|---|---|---|---|---|
| 37 | 1.5 | 0.133 | 12 | 15 |
| 30 | 2.3 | 0.096 | 9 | 21 |
| 24 | 3.0 | 0.064 | 6 | 31 |

By locating the fluid imbibing means within a container, several unique results are obtained. For example, a fluid imbibing means design which normally could be expected to produce one pumping rate can be used to produce various pumping rates by appropriate selection of the operating temperature or by appropriate selection of the fluid in which the imbibing means is immersed. Thus, for example, a pump which is designed to have an output of 1 μl per hour when bathed in an actuating fluid having the osmotic properties of body fluid can produce a higher output when immersed in distilled water and a lower output when immersed in more concentrated saline solution. Further, it is also possible to vary the flow rate of the imbibing means, including a stop-start function, by withdrawing all or a portion of the actuating fluid from the housing or by varying the concentration or composition of the actuating fluid or by varying the area of the fluid imbibing means which is exposed to the actuating fluid, or any combination of the above techniques. Examples of housing designs and methods for varying the exposure of the imbibing means to the actuating fluid and for providing a stop-restart function are discussed in U.S. Pat. No. 4,474,575, incorporated herein by reference.

Figure 6:
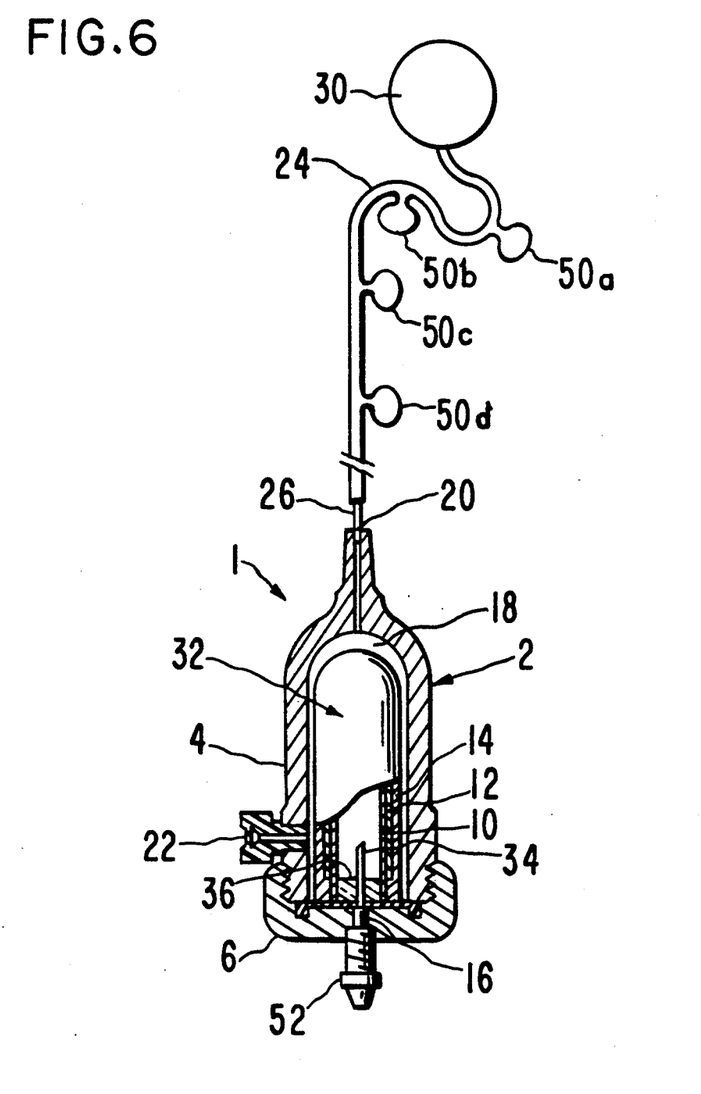
FIG. 6 is a cross-sectional view of another embodiment of the invention.

While the present invention is directed in one preferred embodiment to the collection of body fluids for analysis, in another embodiment the pump 1 may be used to administer an agent such as a drug to an animal, including humans, while concurrently monitoring the body concentrations of the agent or other functions of the body in response to the agent. A configuration useful in the practice of this embodiment is illustrated in FIG. 6. As shown in FIG. 6, in addition to having a connector 26 at the suction port end of the housing 2, there is also a fluid communicating means for conducting fluid from bag 10 of the fluid imbibing means to a situs of use. In the embodiment illustrated in FIG. 6, the fluid communicating means comprises a connecting fitting 52 extending from vent 16. Fitting 52 is adapted for attachment to a hypodermic needle or to a suitable catheter leading to a hypodermic needle. In this embodiment, flexible bag 10, rather than containing air or an inert fluid such as water, holds a drug or other agent that is to be administered to the body.

To operate the pump of FIG. 6, the drug to be dispensed is charged into bag 10. This may be done prior to insertion of the fluid imbibing means into the housing 2, such as when the means is self-contained as is the ALZET ® minipump 32, by means of a hypodermic needle inserted into elastomeric plug 36. Alternately, the drug may be charged into the fluid imbibing means after it is placed in the housing 2 by means of a smaller gauge hypodermic needle inserted within the port in fitting 52 and through vent 16. In filling bag 10, the drug or other agent is injected into bag 10 until drops of fluid appear at the end of fitting 52 to eliminate any air from the interior of the bag. The thus-charged device when used as a medical infusor, depending upon the drug and its stability and any interaction with the material from which flexible bag 10 is formed, may then be stored for varying periods of time, preferably under refrigeration, until it is needed for use. At that time, the pump 1 is actuated by introducing an actuating fluid into space 18 via injection port 22 as described previously hereinabove. As solute layer 12 imbibes the actuating fluid, expansion of the layer causes flexible bag 10 to collapse and to push the drug out through vent 16. Meanwhile, the end of fitting 52 is connected to a hypodermic needle or to a suitable catheter leading to a hypodermic needle, and the needle is inserted at the infusion site on the animal or human to be treated after the pump has been actuating for sufficient time to free the line of air, as evidenced by emission of a substantially constant flow of drug from the needle. Alternately, the pump 1 could be used to deliver fluid to a remote site such as an intravenous (IV) bag or a Y fitting in an IV line to administer the contents of the fluid imbibing means in conjunction with other therapeutic or beneficial agents, for example. At the same time, the sample receiving means, sample tubing 24 for example, is attached to the suction port 20 of pump 1, by means of the connector 26, and to the sample site on the treated animal or human. Sample fluid is then collected at predetermined time intervals, conveniently by means of sample reservoirs 50a–50d for example, to monitor the concentration of drug in the body or to measure other parameters, as desired.

Thus, the invention provides, in a suction pump, a reliable means for obtaining a fluid sample or series of samples from a sample source, and particularly a biological sample from an animal body, at a controlled rate and over a prolonged period of time. In addition, the invention provides a simple and convenient single unit for both administering an agent to an animal and concurrently monitoring the concentration of the agent or other parameters in the animal. Prime advantages of the pump of the invention are that it is simple in construction and simple to use and is small, lightweight and selfcontained, so that it is relatively inexpensive and portable and does not interfere with a donor's normal activities.

While the invention has been described and illustrated with reference to certain preferred embodiments thereof, it should not be construed as being limited thereto. Various modifications, changes, omissions, and substitutions that are obvious to those of skill in the art are intended to be within the scope of the following claims.

What is claimed is:

1. A self-contained suction pump for drawing a fluid comprising:
   a) an impermeable rigid housing;
   b) a fluid imbibing means sealingly mounted within the housing and having an external surface which is at least in part permeable to an actuating fluid;
   c) a space between the outer wall of the fluid imbibing means and the inner wall of the rigid housing adapted to contain an actuating fluid;
   d) an injection port for injecting an actuating fluid in the space between the housing and the fluid imbibing means;
   e) a suction port extending through the rigid housing and in communication with the space between the housing and the fluid imbibing means; and
   f) sample receiving means adapted to be attached to the suction port and to a fluid sample source.

2. A suction pump according to claim 1 wherein the sample receiving means is flexible tubing.

3. A suction pump according to claim 1 wherein the housing comprises a body and a resealable cap.

4. A suction pump according to claim 1 which further comprises a vent extending through the rigid housing and in communication with the interior of the fluid imbibing means.

5. A suction pump according to claim 4 wherein the vent is a venting needle.

6. A suction pump according to claim 4 wherein the sample receiving means is flexible tubing, the housing comprises a body and a resealable cap, and the vent extends through the resealable cap.

7. A suction pump according to claim 1 wherein the fluid imbibing means is a fluid driving member which comprises:
   a) an inner flexible bag;
   b) an intermediate layer of an osmotically effective solute composition at least partly encapsulating the bag; and
   c) an outer shape-retaining membrane encapsulating the intermediate layer, the membrane being at least in part permeable to water.

8. A suction pump according to claim 7 which further comprises a vent extending through the rigid housing and in communication with the interior of the fluid driving member.

9. A suction pump according to claim 8 wherein the vent is a venting needle.

10. A suction pump according to claim 8 wherein the sample receiving means is flexible tubing, the housing comprises a body and a resealable cap, and the vent extends through the resealable cap.

11. A self-contained suction pump for drawing a fluid comprising:
    a) an impermeable rigid housing;
    b) a fluid driving member sealingly mounted within the housing, the driving member comprising:
       i) an inner flexible bag,
       ii) an intermediate layer of an osmotically effective solute composition at least partly encapsulating the bag, and
       iii) an outer shape-retaining membrane encapsulating the intermediate layer, the membrane being at least in part permeable to water;
    c) a vent extending through the rigid housing and in communication with the interior of the driving member;
    d) a space between the inner wall of the rigid housing and the outer wall of the driving member adapted to contain an actuating fluid;

e) an injection port for injecting an actuating fluid in the space between the housing and the driving member;

f) a suction port extending through the rigid housing and in communication with the space between the housing and the driving member; and g) sample receiving means adapted to be attached to the suction port and to a fluid sample source.

12. A suction pump according to claim 11 wherein the housing comprises a body and a resealable cap.

13. A suction pump according to claim 11 wherein the vent is a venting needle.

14. A suction pump according to claim 11 wherein the sample receiving means is flexible tubing, the housing comprises a body and a resealable cap, and the vent extends through the resealable cap.

15. A self-contained suction pump for concurrently delivering a quantity of fluid agent and drawing a fluid sample over a prolonged period of time, the pump comprising:

a) an impermeable rigid housing;

b) a fluid imbibing means for discharging a volume of fluid agent, the fluid imbibing means sealingly mounted within the housing and having an external surface which is at least in part permeable to an actuating fluid;

c) a fluid communicating means for conducting fluid agent from the fluid imbibing means to a situs of use;

d) a space between the outer wall of the fluid imbibing means and the inner wall of the rigid housing adapted to contain an actuating fluid;

e) an injection port for injecting an actuating fluid in the space between the housing and the fluid imbibing means;

f) a suction port extending through the rigid housing and in communication with the space between the housing and the fluid imbibing means; and g) sample receiving means adapted to be attached to the suction port and to a fluid sample source.

16. A suction pump according to claim 15 wherein the sample receiving means is flexible tubing.

17. A suction pump according to claim 15 wherein the housing comprises a body and a resealable cap.

18. A suction pump according to claim 15 wherein the receiving means is flexible tubing and the housing comprises a body and a resealable cap.

19. A method for drawing a sample fluid from a sample source, the method comprising:

a) injecting actuating fluid into a suction pump, the suction pump comprising:

i) an impermeable rigid housing, ii) a fluid imbibing means sealingly mounted within the housing and having an external surface which is at least in part permeable to an actuating fluid, iii) a space between the outer wall of the fluid imbibing means and the inner wall of the rigid housing adapted to contain an actuating fluid, iv) an injection port for injecting an actuating fluid in the space between the housing and the fluid imbibing means, v) a suction port extending through the rigid housing and in communication with the space between the housing and the fluid imbibing means, and vi) sample receiving means adapted to be attached to the suction port and to a fluid sample source;

b) placing the sample receiving means of the suction pump in communication with the sample source;

c) allowing sample fluid from the sample source to be drawn into the sample receiving means; and d) retrieving the sample fluid from the sample receiving means.

20. A method for concurrently delivering a quantity of fluid agent and drawing a fluid sample over a prolonged period of time, the method comprising:

a) charging the fluid agent into fluid imbibing means of a suction pump, the suction pump comprising:

i) an impermeable rigid housing, ii) a fluid imbibing means for discharging a volume of fluid, the fluid imbibing means sealingly mounted within the housing and having an external surface which is at least in part permeable to an actuating fluid, iii) a fluid communicating means for conducting fluid from the fluid imbibing means to a situs of use, iv) a space between the outer wall of the fluid imbibing means and the inner wall of the rigid housing adapted to contain an actuating fluid, v) an injection port for injecting an actuating fluid in the space between the housing and the fluid imbibing means, vi) a suction port extending through the rigid housing and in communication with the space between the housing and the fluid imbibing means, and vii) sample receiving means adapted to be attached to the suction port and to a fluid sample source;

b) injecting actuating fluid into the suction pump;

c) placing the fluid communicating means of the suction pump in communication with the situs of use;

d) placing the sample receiving means of the suction pump in communication with the sample source;

e) allowing sample fluid from the sample source to be drawn into the sample receiving means; and d) retrieving the sample fluid from the sample receiving means.

* * * * *

UNITED STATES PATENT AND TRADEMARK OFFICE
CERTIFICATE OF CORRECTION

PATENT NO. : 5,024,663

DATED : June 18, 1991

INVENTOR(S) : Su Il Yum

It is certified that error appears in the above-identified patent and that said Letters Patent is hereby corrected as shown below:

Delete drawing Sheet 4 of 4 showing FIG. 6 and replace with new Sheet 4 of 4 showing FIG. 2 and FIG. 5 (attached).

Signed and Sealed this

Twenty-eighth Day of April, 1992

Attest:

HARRY F. MANBECK, JR.

*Attesting Officer*  *Commissioner of Patents and Trademarks*